US00PP24407P3

(12) United States Plant Patent
Caster et al.

(10) Patent No.: US PP24,407 P3
(45) Date of Patent: Apr. 29, 2014

(54) BLUEBERRY PLANT NAMED 'DRISBLUEFOUR'

(50) Latin Name: ***Vaccinium corymbosum* L.**
Varietal Denomination: DrisBlueFour

(75) Inventors: Brian K. Caster, Salinas, CA (US); Jennifer K. Izzo, Watsonville, CA (US); Arlen Draper, Payson, AZ (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 60 days.

(21) Appl. No.: 13/573,345

(22) Filed: Sep. 11, 2012

(65) Prior Publication Data

US 2014/0075617 P1 Mar. 13, 2014

(51) Int. Cl.
*A01H 5/00* (2006.01)
*A01H 4/00* (2006.01)
*A01H 5/08* (2006.01)

(52) U.S. Cl.
CPC .. *A01H 5/00* (2013.01); *A01H 4/00* (2013.01); *A01H 5/08* (2013.01)
USPC ..... Plt./157

(58) Field of Classification Search
CPC ..... A01H 5/08; A01H 5/00; A01H 4/00
USPC ..... Plt./157
See application file for complete search history.

*Primary Examiner* — Annette Para
(74) *Attorney, Agent, or Firm* — Jondle Plant Sciences Division of Swanson & Bratschun, L.L.C.

(57) ABSTRACT

A new and distinct variety of blueberry plant named 'DrisBlueFour' particularly distinguished by having a very low chilling requirement, high productivity and firm, sweet berries with intense blue color and aromatic flavor, is disclosed.

2 Drawing Sheets

Genus and species: *Vaccinium corymbosum* L.
Variety denomination: 'DrisBlueFour'.

BACKGROUND OF THE NEW PLANT

The invention relates to a new and distinct blueberry variety designated 'DrisBlueFour' and botanically known as *Vaccinium corymbosum* L. This new blueberry variety was discovered in Santa Cruz, Calif. in June 2000 and originated from a cross between the proprietary female parent blueberry plant 'FL 97-26' (unpatented) and the male parent blueberry plant 'MS139' (unpatented). The original seedling of the new variety was first asexually propagated at a nursery in Monterey, Calif. 'DrisBlueFour' was subsequently asexually propagated and underwent further testing at a nursery in Santa Cruz, Calif. for twelve years. The present invention has been found to be stable and reproduce true to type through successive asexual propagations via softwood cuttings.

Plant Breeder's Rights for this variety have not been applied for. 'DrisBlueFour' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz, Calif.

1. A very low chilling requirement;
2. High productivity; and
3. Firm, sweet berries with intense blue color and aromatic flavor.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are 12 years old.

DESCRIPTION OF THE NEW CULTIVAR

Figure 1:
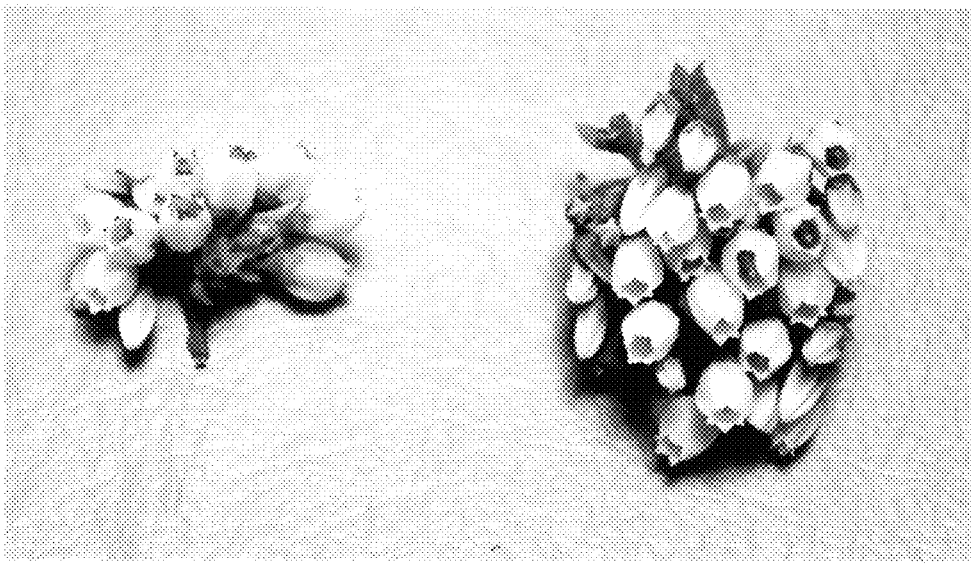
FIG. 1 shows a close-up of the mature flowers.
Figure 2:
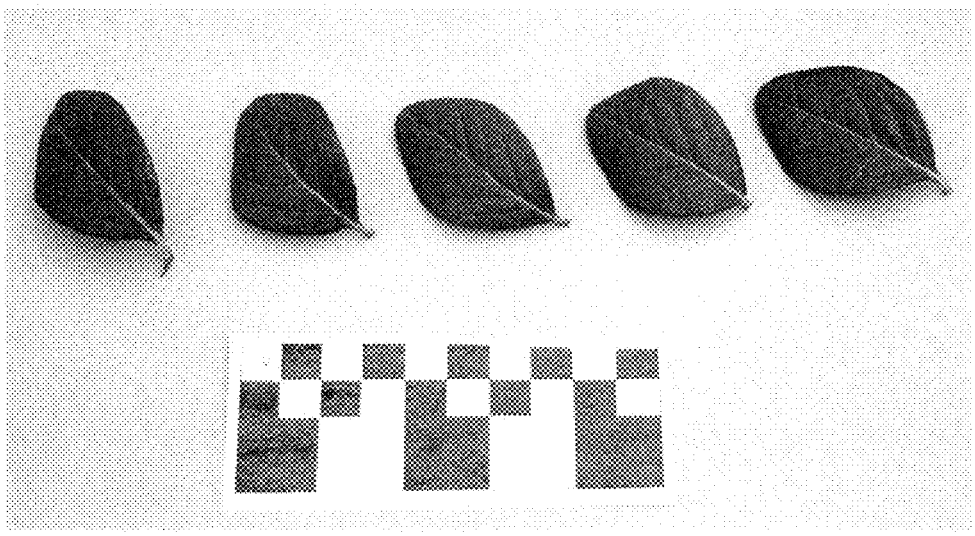
FIG. 2 shows a close-up of the leaves.
Figure 3:
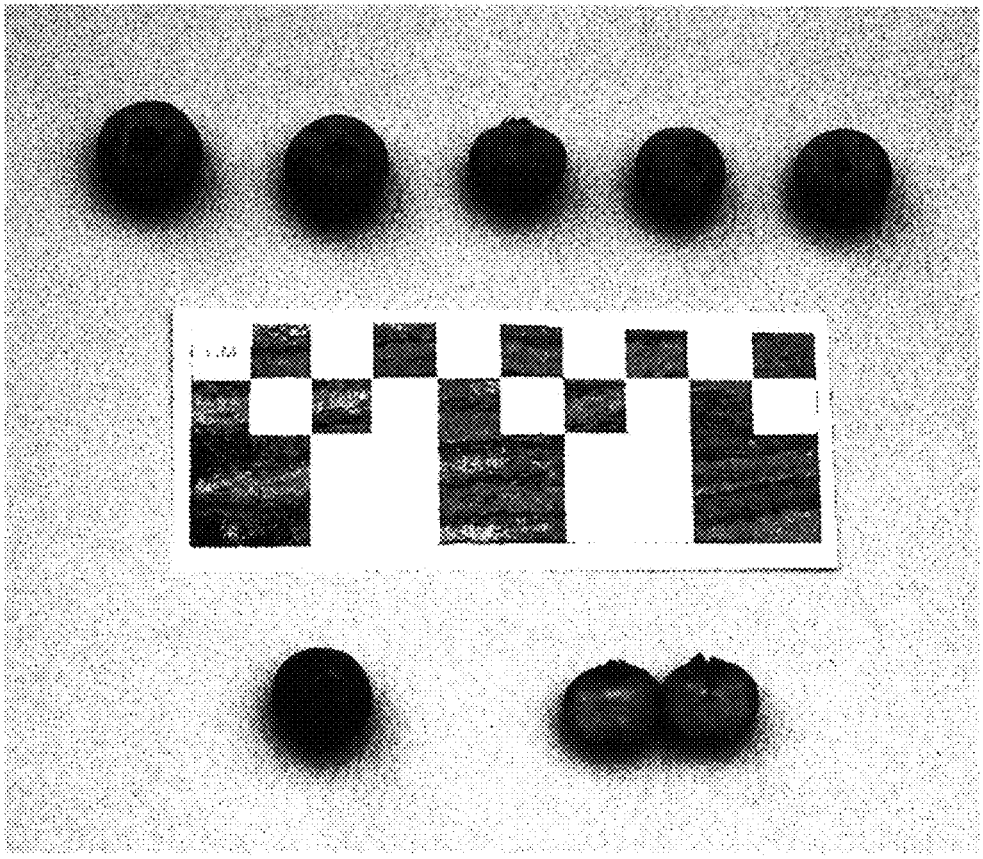
FIG. 3 shows a close-up of the whole fruit and a cross-section of the fruit.

The following detailed description sets forth the distinctive characteristics of 'DrisBlueFour.' The data which define these characteristics is based on observations taken in Santa Cruz, Calif. from 2000-2012. This description is in accordance with UPOV terminology. Color designations, color descriptions, and other phenotypical descriptions may deviate from the stated values and descriptions depending upon variation in environmental, seasonal, climatic and cultural conditions. 'DrisBlueFour' has not been observed under all possible environmental conditions. The botanical description of 'DrisBlueFour' was taken from 12 year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:

*Family.*—Ericaceae.
*Botanical.*—*Vaccinium corymbosum* L.
*Common name.*—Blueberry.
*Variety name.*—'DrisBlueFour'.

Parentage:

*Female parent.*—The proprietary blueberry plant 'FL 97-26' (unpatented).

*Male parent.*—The blueberry plant 'MS139' (unpatented).

Plant:

*Size.*—Medium.

*Height.*—109.4 cm.

*Width.*—129.9 cm.

*Length/width ratio.*—0.8.

*Plant vigor.*—Medium to strong.

*Growth habit.*—Semi-erect.

*Productivity.*—High.

*Cold hardiness.*—Medium.

*Chilling requirement.*—Very low; 150-250 chilling hours.

*Propagation.*—Soft wood cuttings.

*Time of vegetative bud burst.*—Early to medium.

*Fruiting type.*—Only on one-year-old shoots.

*Cane renewal.*—Medium.

*Internode length* (*upper half on one-year old shoot*).—30.29 mm.

*One-year old canes* (*young canes*).—Length: 74.17 cm. Diameter at the base: 9.67 mm. Diameter at the tip: 4.15 mm. Texture: Smooth. Color (One-year old shoot, branch and canes): RHS 145A (Medium yellow-green).

*Five-year old canes* (*mature canes*).—Length: 114.05 cm. Diameter at the base: 18.70 mm. Diameter at the tip: 4.76 mm. Texture: Rough. Color: RHS 197B (Medium greyed-green).

Leaves:

*Length.*—Medium; 5.12 cm.

*Width.*—Medium; 3.06 cm.

*Length/width ratio.*—1.7; longer than broad.

*Shape.*—Elliptic.

*Apex.*—Cuspidate.

*Base.*—Obtuse.

*Margin.*—Entire.

*Glossiness.*—Medium.

*Pubescence.*—Glabrous (Absent).

*Sheath.*—Absent.

*Arrangement.*—Alternate.

*Venation.*—Reticulate.

*Color.*—Upper surface: Dark; RHS 147A (Dark yellow-green). Lower surface: Medium; RHS 147C (Medium yellow-green).

*Appearance of leaf bud.*—Medium.

*Internode length* (*one-year old shoot, upper half*).—Medium; 11.38 mm.

Petiole:

*Length.*—4.3 mm.

*Diameter.*—1.73 mm.

*Color.*—RHS 144C (Medium yellow-green).

Flowers:

*Length* (*excluding peduncle*).—Medium; 8.36 mm.

*Diameter.*—6.19 mm.

*Length/width ratio.*—1.4.

*Color.*—RHS 155D (White).

*Flower bud.*—Length: 8.3 mm. Width: 3.4 mm. Number of flowers per bud: 7. Color on mature buds: RHS 65C (Light red-purple) and RHS 155B (White).

*Petal width.*—3.75 mm.

*Fragrance.*—Faint.

*Time of beginning flowering on one-year shoot.*—Medium.

*Time of flowering* (50% *full bloom*).—Early; March 15.

*Pedicel.*—Length: 7.27 mm. Diameter: 1.08 mm. Color: RHS 142C (Light green).

*Corolla.*—Aperture diameter: 2.42 mm. Shape: Urceolate (Urn-shaped). Size of corolla tube: Medium. Corolla tube color: Very weak or absent; RHS N155C (White). Ridges on tube: Present.

*Peduncle length.*—24.83 mm.

Reproductive organs:

*Style length* (*including stigma*).—Medium; 8.23 mm.

*Style color.*—RHS 144B (Medium yellow-green).

*Ovary color.*—RHS 189B (Medium greyed-green).

*Pollen amount.*—Low.

*Pollen color.*—RHS 4D (Light yellow).

*Anther color.*—RHS N170B (Medium greyed-orange).

Fruit:

*Size.*—Medium to large.

*Length.*—13.93 mm.

*Width.*—15.10 mm.

*Length/width ratio.*—0.9.

*Fruit pedicel diameter.*—1.01 mm.

*Weight.*—2.5 g.

*Number of berries per cluster.*—7.

*Cluster density.*—Medium.

*Shape in longitudinal sections.*—Oblate.

*Intensity of green color* (*immature fruit with bloom*).—Medium; RHS 191B (Medium greyed-green).

*Color of skin* (*immature fruit without bloom*).—RHS 145A (Medium yellow-green).

*Color of skin* (*mature fruit without bloom*).—RHS N186A (Dark greyed-purple).

*Color of skin* (*mature fruit with bloom*).—RHS 98D (Light blue).

*Intensity of bloom* (*mature fruit*).—Very strong.

*Attitude of sepals.*—Incurving and erect.

*Calyx.*—Diameter of basin: Medium; 5.78 mm. Depth of basin: Medium; 2.97 mm. Diameter/depth ratio: 1.9.

*Flesh color.*—RHS 145C (Light yellow-green).

*Firmness.*—Firm.

*Sweetness.*—Medium.

*Acidity.*—Low.

*Time of beginning of fruit ripening* (*one-year old shoots*).—Early to medium.

*Harvest season.*—Medium.

*Harvest interval.*—May 26-July 22.

Seeds:

*Length.*—1.37 mm.

*Width.*—0.99 mm.

*Length/width ratio.*—1.4.

*Abundance.*—High.

*Color.*—RHS 165A (Dark orange-brown).

Resistance to pests and diseases: Data not available.

COMPARISON WITH COMMERCIAL VARIETIES

'DrisBlueFour' differs from the commercial variety 'DrisBlueOne' (U.S. Plant Pat. No. 20,449) in that 'DrisBlueFour' has leaves with a cuspidate apex and berries weighing 2.5 g with low acidity, whereas 'DrisBlueOne' has leaves with a broadly acute apex and berries weighing 1.7 g with medium acidity. Additionally, 'DrisBlueFour' has a very low chilling requirement, whereas 'DrisBlueOne' has a medium chilling requirement.

'DrisBlueFour' differs from the commercial variety 'DrisBlueTwo' (U.S. Plant Pat. No. 20,488), in that 'DrisBlueFour' has leaves with an obtuse base and an entire margin, whereas 'DrisBlueTwo' has leaves with a broadly acute base and a serrulate margin. Additionally, 'DrisBlueFour' has oblate shaped berries with low acidity, whereas 'DrisBlueTwo' has nearly spherical shaped berries with medium acidity.

We claim:

1. A new and distinct variety of blueberry plant named 'DrisBlueFour' as shown and described herein.

* * * * *